US012594364B2

(12) United States Patent (10) Patent No.: US 12,594,364 B2
Assell et al. (45) Date of Patent: Apr. 7, 2026

(54) BONE VOID FILLER PREPARATION SYSTEM

(71) Applicants: ForCyte Medical, LLC, Marietta, GA (US); The Cleveland Clinic Foundation, Cleveland, OH (US)

(72) Inventors: Robert Assell, Minneapolis, MN (US); Andrew Freeman, Minneapolis, MN (US); George Muschler, Cleveland Heights, OH (US)

(73) Assignees: ForCyte Medical, LLC, Marietta, GA (US); The Cleveland Clinic Foundation, Cleveland, OH (US)

( * ) Notice: Subject to any disclaimer, the term of this patent is extended or adjusted under 35 U.S.C. 154(b) by 223 days.

(21) Appl. No.: 18/134,274

(22) Filed: Apr. 13, 2023

(65) Prior Publication Data

US 2023/0241292 A1 Aug. 3, 2023

Related U.S. Application Data

(60) Division of application No. 17/209,604, filed on Mar. 23, 2021, now Pat. No. 11,850,326, which is a continuation of application No. 16/666,170, filed on Oct. 28, 2019, now Pat. No. 10,953,134, which is a continuation of application No. 15/698,588, filed on Sep. 7, 2017, now Pat. No. 10,456,502.

(60) Provisional application No. 62/384,377, filed on Sep. 7, 2016.

(51) Int. Cl.
*A61L 27/38* (2006.01)
*A61B 17/88* (2006.01)
*A61L 27/46* (2006.01)

(52) U.S. Cl.
CPC ...... *A61L 27/3847* (2013.01); *A61B 17/8833* (2013.01); *A61L 27/3821* (2013.01); *A61L 27/46* (2013.01); *A61L 2430/02* (2013.01)

(58) Field of Classification Search
CPC .. A61L 27/38; A61L 27/3874; A61L 27/3847; A61L 27/46; A61L 27/3821; A61L 27/50; A61L 27/425
See application file for complete search history.

(56) References Cited

U.S. PATENT DOCUMENTS

| | | | |
|---|---|---|---|
| 4,969,870 A | 11/1990 | Kramer |
| 5,152,763 A | 10/1992 | Johnson |
| 5,269,785 A | 12/1993 | Bonutti |
| 5,456,267 A | 10/1995 | Stark |
| 5,807,353 A | 9/1998 | Schmitz |
| 5,824,084 A | 10/1998 | Muschler |
| 6,022,354 A | 2/2000 | Mercuri |
| 6,049,026 A | 4/2000 | Muschler |
| 6,132,448 A | 10/2000 | Perez |
| 6,406,454 B1 | 6/2002 | Hajianpour |
| 6,673,629 B2 | 1/2004 | Yoshimura |
| 6,723,131 B2 | 4/2004 | Muschler |
| 6,981,948 B2 | 1/2006 | Pellegrino |
| 8,109,919 B2 | 2/2012 | Kraft |
| 8,137,408 B2 | 3/2012 | Kadiyala |
| 8,343,133 B2 | 1/2013 | Allee |
| 8,439,929 B1 | 5/2013 | Sharratt |
| 8,579,912 B2 | 11/2013 | Isaza |
| 8,852,119 B2 | 10/2014 | Wawrzyniak |
| 2002/0058945 A1 | 5/2002 | Steiner |
| 2002/0082519 A1 | 6/2002 | Miller |
| 2002/0161449 A1 | 10/2002 | Muschler |
| 2003/0031695 A1 | 2/2003 | Kadiyala |
| 2004/0071668 A1 | 4/2004 | Barry |

(Continued)

FOREIGN PATENT DOCUMENTS

| | | | |
|---|---|---|---|
| DE | 19949866 A1 | 11/2001 | |
| WO | 1999/59500 A2 | 11/1999 | |
| WO | WO-9959500 A2 * | 11/1999 | ........... A61F 2/4644 |

OTHER PUBLICATIONS

McLain, et al. "Transpedicular aspiration of osteoprogenitor cells from the vertebral body: progenitor cell concentration affected by serial aspiration", The Spine Journal, Oct. 19, 2009, vol. 9, No. 12, pp. 995-1002.

Duguy N., et al.: "Biomaterials and osseous regeneration", Annales De Chirurgie Plastique Esthetique, Expansion Scientifique Francaise, Paris, France, vol. 45, No. 3, Jun. 1, 2000, pp. 364-376, Issn: 0294-1260.

Ripamonti U., et al., "Tissue Engineering of Bone by Osteoinductive Biomaterials", MRS Bulletin, Pittsburgh, US, vol. 21, No. 11, Nov. 1, 1996, XP008005014, pp. 36-39.

(Continued)

*Primary Examiner* — Micah Paul Young
(74) *Attorney, Agent, or Firm* — Spencer Fane LLP

(57) ABSTRACT

A bone void filler preparation system that includes a processing vessel, a processing cover, a bone void filler preparation container and tubing. The processing vessel has a recess formed therein. The processing vessel is adapted to receive bone marrow aspirate. The processing cover includes an outer wall, a central wall member and a connection port. The outer wall has an upper edge and a lower edge. The central wall member extends inwardly from the outer wall intermediate the upper and lower edges of the processing cover. The central wall member has an aperture formed therein. The central wall member has a downwardly directed portion that defines an air-retaining region. The air-retaining region is closer to the outer wall upper edge than the aperture. The connection port is operably connected to the aperture. The processing cover is movable in the processing cover recess. The bone void filler preparation container has an inlet portion and an outlet port. The bone void filler preparation container is adapted to receive a bone void filler matrix therein. The tubing fluidly connects the processing cover connection port and the bone void filler preparation container inlet port.

20 Claims, 4 Drawing Sheets

(56)　　　　　References Cited

U.S. PATENT DOCUMENTS

| | | |
|---|---|---|
| 2005/0101963 A1 | 5/2005 | Merboth |
| 2005/0130301 A1 | 6/2005 | McKay |
| 2006/0246150 A1 | 11/2006 | Thorne |
| 2006/0264964 A1 | 11/2006 | Scifert |
| 2007/0055282 A1 | 3/2007 | Muschler |
| 2007/0198043 A1 | 8/2007 | Cox |
| 2008/0103605 A1 | 5/2008 | Kadiyala |
| 2008/0145392 A1 | 6/2008 | Knaack |
| 2008/0195115 A1 | 8/2008 | Oren |
| 2008/0288006 A1 | 11/2008 | Brannon |
| 2009/0014391 A1 | 1/2009 | Leach |
| 2009/0081689 A1 | 3/2009 | Yamanishi |
| 2009/0137927 A1 | 5/2009 | Miller |
| 2009/0187116 A1 | 7/2009 | Noishiki |
| 2009/0287190 A1 | 11/2009 | Shippert |
| 2011/0257557 A1 | 10/2011 | Pesce |
| 2012/0116247 A1 | 5/2012 | Wawrzyniak |
| 2013/0030547 A1 | 1/2013 | Burkinshaw |
| 2013/0131545 A1 | 5/2013 | Azimpoor |
| 2014/0100574 A1 | 4/2014 | Bono |
| 2014/0105960 A1 | 4/2014 | Zoldan |
| 2014/0257133 A1 | 9/2014 | Andrigan |
| 2014/0274894 A1 | 9/2014 | Leach |
| 2014/0363403 A1 | 12/2014 | Segina |
| 2015/0110890 A1* | 4/2015 | Assell ................. A61L 27/3834 424/549 |
| 2015/0164949 A1 | 6/2015 | Sowemimo-Coker |
| 2015/0182268 A1 | 7/2015 | Donner |
| 2016/0325018 A1 | 11/2016 | Assell |
| 2016/0331878 A1 | 11/2016 | McGillicuddy |
| 2018/0353206 A1 | 12/2018 | Assell |

OTHER PUBLICATIONS

Kurita, et al., "Differential Effects of Three Preparations of Human Serum on Expansion of Various Types of Human Cells", American Society of Plastic Surgeons, Dec. 20, 2007, 12 pgs.
International Search Report and Written Opinion received for PCT Serial No. PCT/US2021/018570 on May 7, 2021, 9 pgs.

* cited by examiner

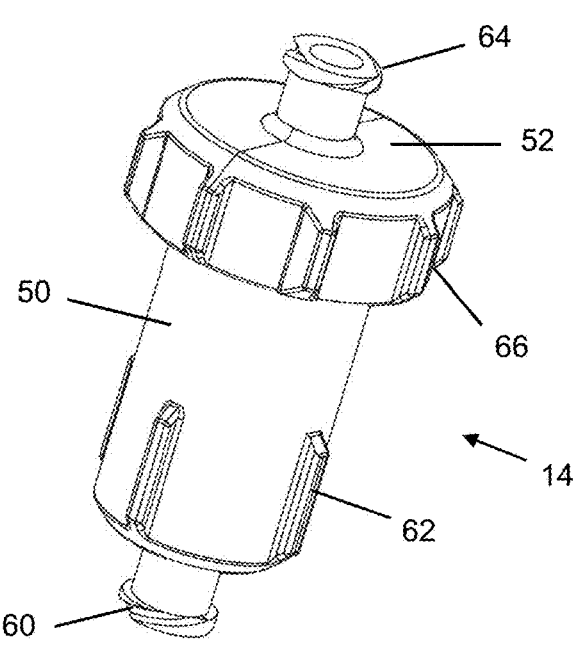
Fig. 4
Fig. 5
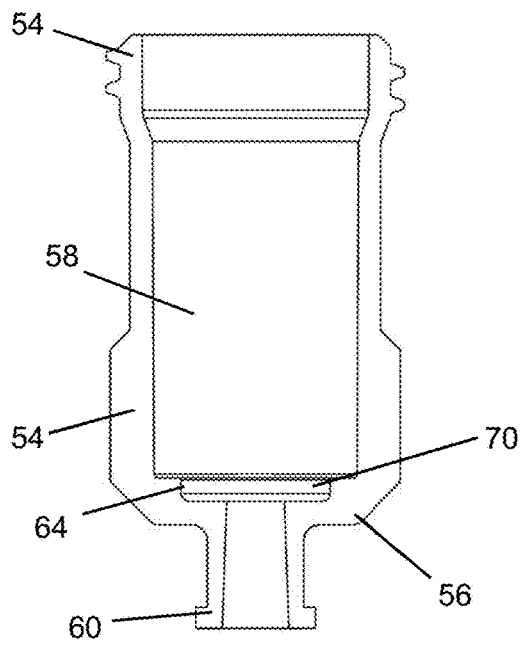
Fig. 6
Fig. 7

BONE VOID FILLER PREPARATION SYSTEM

REFERENCE TO RELATED APPLICATION

This application is a divisional of U.S. application Ser. No. 17/209,604, filed on Mar. 23, 2021, which is a continuation of U.S. application Ser. No. 16/666,170, filed on Oct. 28, 2019, which is a continuation of U.S. application Ser. No. 15/698,588, filed on Sep. 7, 2017, and claims priority to Provisional Application No. 62/384,377, filed on Sep. 7, 2016, the contents of which are incorporated herein by reference.

FIELD OF THE INVENTION

The invention relates generally to preparing bone void fillers. More particularly, the invention relates to a bone void filler preparation method.

BACKGROUND OF THE INVENTION

In the US, bone grafts are most commonly used in spinal fusion surgery and, more generally, in the fusion or arthrodesis of any skeletal joint. In addition, bone graft is generally used in trauma surgery for the treatment of fresh fractures and non-unions, which are typically identified as fractures within 6 months that have not healed properly. The bone graft materials typically bridge a gap between bone segments and may also provide a three-dimensional scaffold on which the bone can grow.

Bone graft treatment is also typically used in conjunction with fresh fractures where the bone has been shattered or where the patient is at a very high risk of developing a non-union fracture. Because many fractures are not this severe and can be treated with alternative methods of fixation, bone grafts are not frequently needed during fresh fracture treatments.

Two areas where bone grafts are used are in conjunction with joint reconstruction and joint revision. For example, the bone graft may be used to fill a void between the bone and joint implant in a joint reconstruction surgery. Joint revision is much more likely to need a bone graft because a large void may result from the removal of the original implant. Joint revisions that use bone graft material therefore usually require a relatively large quantity of the bone graft material.

There are different types of bone graft materials that may be used to assist a patient's body in bone regeneration. These bone graft materials are typically classified as either natural or synthetic materials.

Natural bone graft materials are classified in the following groups: Autograft is bone graft material that is obtained from the same individual that will receive the bone graft material. Allograft is bone graft material that is obtained from another human source, which typically is from cadavers. Xeongraft is bone graft material that is obtained from another species.

Bone grafts can also be categorized by their bone-forming properties as osteoconductive, osteoinductive or osteogenic. Osteoconductivity is the ability of a material to provide an appropriate scaffold or matrix upon which new bone tissue can form. Osteoinductivity is the ability of a material to stimulate the patient's own system to form new bone. Osteogenic material generates new bone tissue itself. Osteoblasts, which can be found in bone marrow and mesenchymal cells, are the only cells that can create new bone.

Autograft bone has historically been the standard of care because of its osteoconductive, osteoinductive and osteogenic properties. At the time of surgery, bone is taken from a donor site in the patient, often the iliac crest bone but others are used, and then is re-implanted back into the patient at the surgical site.

Autograft is often not used, because obtaining the graft generally requires a second surgical procedure with associated risks and expenses. The autograft also typically results in significant post-operative issues, most significantly pain. An additional type of autograft, concentrated cells from bodily fluids such as blood or bone marrow, is often used as well.

In addition to autograft, many other types of bone graft are used, including processed cadaver bone, i.e., allograft, in the form of demineralized bone matrix, and also so-called "living cell" or "stem cell" allograft. Additionally, constituents known to be involved in new bone formation, such as bone morphogenic proteins, typically produced by recombinant processing means, are used. Synthetic materials such as tricalcium phosphate, calcium sulphate, hydroxyapatite and others are used as well.

| Summary of Bone Graft Characteristics by Material | | | |
|---|---|---|---|
| Type | Osteo-conductive | Osteo-inductive | Osteo-genic |
| Autograft | Yes | Yes | Yes |
| Bone morphogenic proteins | No | Yes (strong) | No |
| Demineralized bone matrix | Yes | Minimal | No |
| Allogeneic stem cell | Yes | Unknown | Yes |
| Bone marrow aspirate | No | Yes (strong) | Yes |
| Synthetics | Yes | No | No |

Bone graft substitutes also fall within the classification of bone filler materials. Examples of bone graft substitutes include collagen, polymers, such as silicone, and some acrylics, hydroxyapatite, calcium sulfate and ceramics.

Bone cement (such as polymethylmethacylate) can be used as a bone void filler to treat bone voids or defects. For example, the bone cement can be used to repair fractured bones and vertebral bodies. The bone cement can be used either in procedures that involve direct injection of the bone cement into the fractured vertebral body (i.e., vertebroplasty) or injection of the bone cement into the vertebral body after the height of the vertebral body is restored using a pressurized balloon (i.e., kyphoplasty).

One of the disadvantages of using bone cement is that, once it is injected inside the patient, the bone cement is an inorganic material and, as such, is treated as a foreign body. As such, the bone cement may not only negatively impact healing but can also lead to bone disease.

Additionally, the bone cement is typically stiffer than bone, which may increase the incidence of adjacent level fractures in the spine. Bone cement leakage may cause complications, and has been reported to occur in vertebroplasty and kyphoplasty procedures. If leakage does occur, the bone cement can cause soft tissue injury due to the high temperatures of the exothermic polymerization reaction. In addition, if the bone cement is forced into the vascular system, it can cause emboli.

Bone marrow and bone marrow aspirate concentrate are considered to have a significantly higher bioactivity than circulating blood or concentrated blood known as platelet rich plasma. These features mean that bone marrow is often viewed as being superior to platelet rich plasma for use in orthopedic applications such as spinal fusion and trauma surgery because the bone marrow contains progenitor cells and multipotent stem cells, which assist in the formation of new bone.

Bone marrow aspirate concentrate has become increasingly popular in bone growth applications, particularly spinal fusion and trauma surgery, because of its osteogenic properties. Traditionally, autograft was the gold standard grafting material in these procedures due to the presence of osteoblasts and osteogenic precursor cells, as well as its osteoconductive and osteoinductive properties.

To avoid the risks associated with autograft procurement, such as donor site infection and morbidity, bone marrow aspirate concentrate has been increasingly used because it has properties that are similar to autograft and allows surgeons and patients to avoid autograft procurement.

Muschler, U.S. Pat. Nos. 5,824,084 and 6,049,026, both disclose systems for preparing a bone graft in which a bone marrow suspension is passed through a porous, biocompatible, implantable matrix. Muschler indicates that the bone graft can be prepared intraoperatively for use in a person from which the bone graft aspirate was obtained.

Muschler, U.S. Pat. No. 6,723,131, discloses a system for preparing bone graft. A porous, biocompatible, implantable matrix is placed in a hollow column having caps at opposite ends. Bone marrow aspirate is placed in a syringe, which is attached to one of the caps, and then the syringe is used to urge the bone marrow aspirate through the porous, biocompatible, implantable matrix.

SUMMARY OF THE INVENTION

An embodiment of the invention is directed to a bone void filler preparation system that includes a processing vessel, a processing cover, a bone void filler preparation container and tubing. The processing vessel has a recess formed therein. The processing vessel is adapted to receive bone marrow aspirate. The processing cover includes an outer wall, a central wall member and a connection port. The outer wall has an upper edge and a lower edge. The central wall member extends inwardly from the outer wall intermediate the upper and lower edges of the processing cover. The central wall member has an aperture formed therein. The central wall member has a downwardly directed portion that defines an air-retaining region. The air-retaining region is closer to the outer wall upper edge than the aperture. The connection port operably connected to the aperture, wherein the processing cover is movable in the processing cover recess. The bone void filler preparation container has an inlet portion and an outlet port. The bone void filler preparation container is adapted to receive a bone void filler matrix therein. The tubing fluidly connects the processing cover connection port and the bone void filler preparation container inlet port.

Another embodiment of the invention is directed to a process of preparing bone void filler. A processing vessel is provided that has a recess formed therein. A processing cover is provided that includes an outer wall, a central wall member and a connection port. The outer wall has an upper edge and a lower edge. The central wall member extends inwardly from the outer wall intermediate the upper and lower edges of the processing cover. The central wall member has an aperture formed therein. The central wall member has a downwardly directed portion that defines an air-retaining region. The air-retaining region is closer to the outer wall upper edge than the aperture. The connection port operably is connected to the aperture. A bone void filler preparation container is provided that has an inlet portion and an outlet port. The processing cover connection port and the bone void filler preparation container inlet port are fluidly connected with tubing. Bone void filler matrix is placed in the bone void filler preparation container. Bone marrow aspirate is placed in the processing vessel. The processing cover is placed in the processing vessel so that air is retained in the air-retaining region and so that at least a portion of the processing cover is above an upper surface of the bone marrow aspirate. The bone void filler preparation container outlet port is used to draw the bone marrow aspirate through the processing cover aperture, the tubing and the bone void filler matrix. Progenitor cells from the bone marrow aspirate are retained in the bone void filler matrix to form bone void filler.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 4 is a perspective view of a bone void filler preparation chamber for use in the bone void filler processing system.

FIG. 5 is a sectional view of the bone void filler preparation chamber taken along a line 5-5 in FIG. 4.

FIG. 6 is a perspective view of the bone void filler preparation chamber with a cover removed therefrom.

FIG. 7 is a sectional view of the bone void filler preparation chamber with a cover removed therefrom taken along a line 7-7 in FIG. 6.

DETAILED DESCRIPTION OF THE INVENTION

Figure 1:
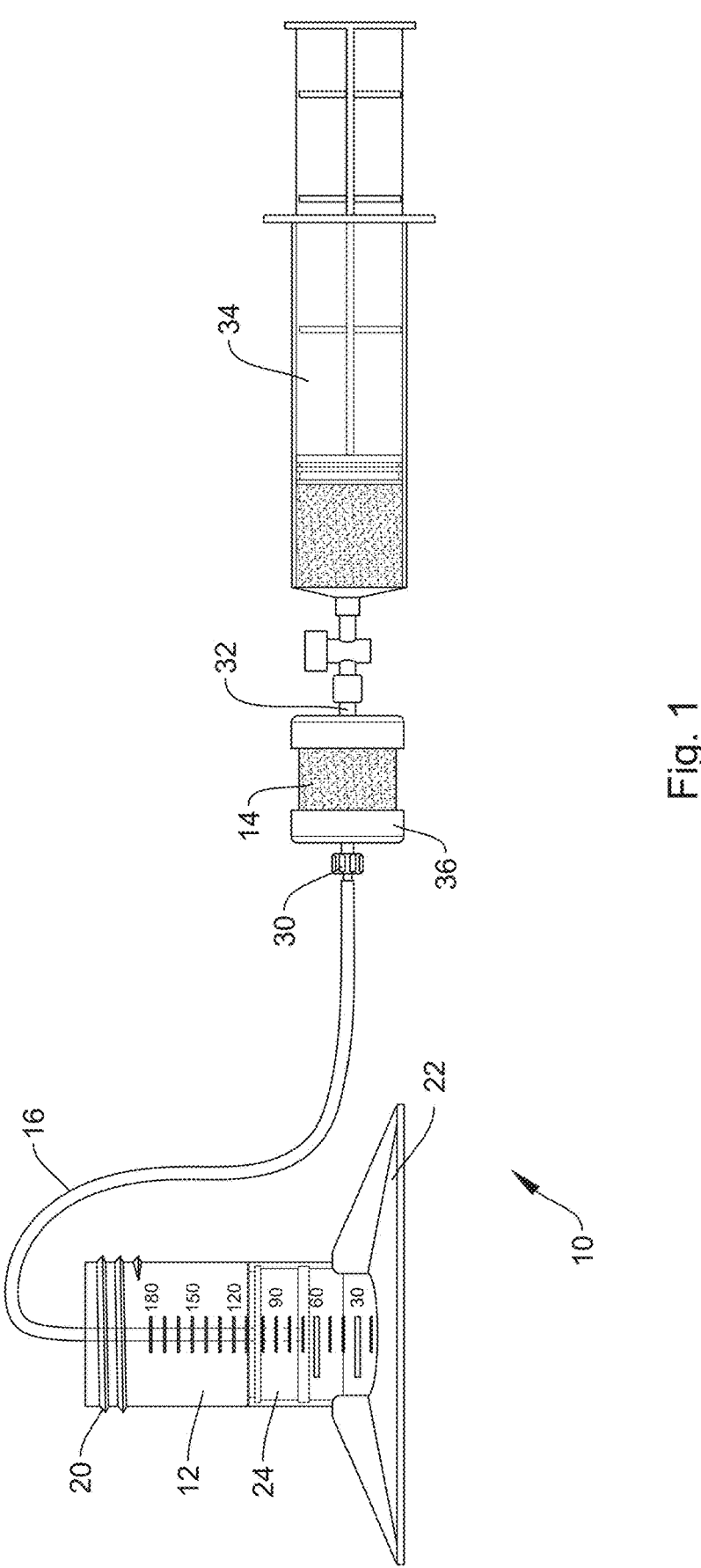
FIG. 1 is a side view of a bone void filler processing system according to an embodiment of the invention.

An embodiment of the invention is directed to a bone void filler preparation system, which is illustrated in FIG. 1. The bone void filler preparation system 10 generally includes a processing vessel 12 that is operably attached to a bone void filler preparation chamber 14 with tubing 16.

The processing vessel 12 receives bone marrow aspirated from a patient. In other embodiments, the processing vessel 12 also receives bone fragments aspirated from the patient along with the bone marrow. The bone fragments may be separated from the bone marrow such as being retained in a collection vessel (not shown) that is operably attached to the processing vessel. Such a configuration is described in U.S. application Ser. No. 15/150,089, which is assigned to the assignee of the present application, the contents of which are incorporated herein by reference.

One potential device and process for aspirating bone fragments and bone marrow from the patient is described in U.S. application Ser. No. 15/150,121, which is assigned to the assignee of the present application, the contents of which are incorporated herein by reference.

The invention thereby facilitates recovery of a large percentage of the beneficial cells that are aspirated from the patient such that the recovered beneficial cells can used in preparing the bone void filler. In particular, the invention enables a high recovery of stem and progenitor cells.

In certain embodiments, the processing vessel 12 has a generally cylindrical recess formed therein into which the bone marrow is collected after being aspirated from the patient. The volume of the processing vessel 12 is selected based upon the bone marrow that is desired to be aspirated from the patient. In certain embodiments, the volume of the processing vessel 12 is between about 100 milliliters and about 200 milliliters.

Proximate an upper end of the processing vessel 12, a connection mechanism 20 may be provided on the processing vessel 12. In certain embodiments, the connection mechanism 20 is a thread that extends from an outer surface of the processing vessel 12. The connection mechanism 20 facilitates attachment of a cover (not shown) to the processing vessel 12. The cover may be used in conjunction with the process of extracting the bone marrow from the patient. In other embodiments, the cover is used in conjunction with the processing vessel 12 during the process of recovering the beneficial cells from the bone marrow. A potential advantage of using the cover is to prevent the bone marrow spilling from the processing vessel 12 if the processing vessel is inadvertently knocked over.

Another mechanism that can be utilized to minimize the potential of the processing vessel 12 being knocked over is to place the processing vessel 12 in a base 22 that has a width that is greater than the width of the processing vessel 12. In certain embodiments, the base 22 has a width that is at least about two times the width of the processing vessel 12.

A processing cover 24 may be used in conjunction with withdrawing a portion of the bone marrow from the processing vessel 12. In certain embodiments, the processing cover 24 is slidably movable in the processing vessel 12. The processing cover 24 thereby substantially encloses an upper end of the processing vessel 12 while facilitating changing of the volume enclosed therein.

The processing cover 24 thereby has a shape that generally conforms to the shape of the processing vessel 12 but is formed with a diameter that is slightly smaller than the inner diameters of the processing vessel 12.

The processing cover 24 is fabricated from a material that is less dense than the bone marrow fluid such that as the bone marrow is collected in the processing vessel 12 increases, the processing cover 24 raises in the processing vessel 12. In one such embodiment, the processing cover 24 is substantially hollow.

The processing cover 24 has a height that is sufficiently large so that the processing cover 24 is restricted to moving in a generally vertical direction. In one such embodiment, a height of the processing cover 24 is at least about ⅓ of an inner diameter of the processing vessel 12.

In other embodiments, the diameter of the processing cover 24 is about two times larger than the height of the processing cover 24. Using such a configuration minimizes the potential of the processing cover 24 becoming wedged in the processing vessel 12 instead of moving vertically.

The processing cover 24 has a connection port on an upper surface thereof. The connection port facilitates attachment of tubing 16 to the processing cover 24. The processing cover 24 also includes a bore (shown with dotted lines) that extends from the connection port to a lower surface of the processing cover 22. The configuration of the processing cover 24 thereby facilitates withdrawing material in the processing vessel 12 through the tubing 16. This process causes the material in the processing vessel 12 that is proximate the processing cover 24 to be withdrawn through the tubing 16. As the material is withdrawn from the processing vessel 12, the processing cover 24 lowers in the processing vessel 12.

Figure 2:
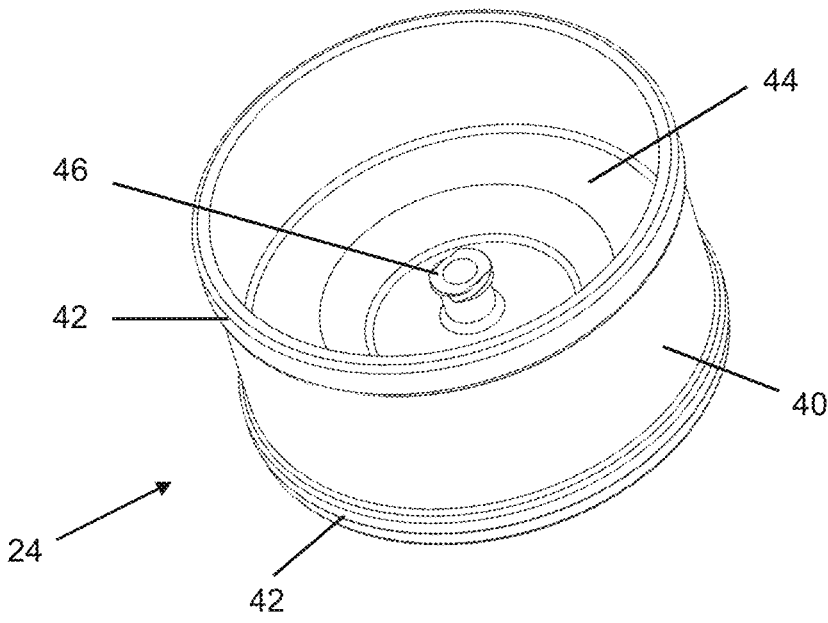
FIG. 2 is a perspective view of a processing cover for use in the bone void filler processing system.
Figure 3:
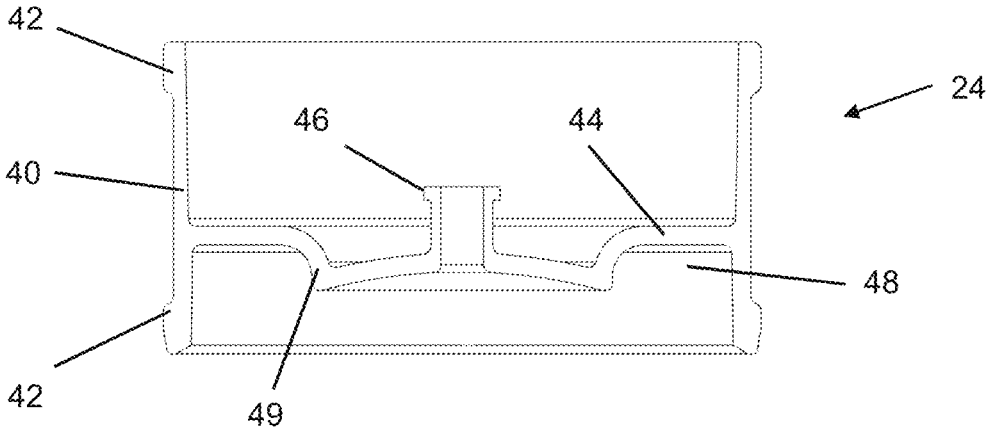
FIG. 3 is a sectional view of the processing cover taken along a line 3-3 in FIG. 2.

Additional details on the shape of the processing cover 24 are set forth in FIGS. 2 and 3. One of the challenges in fabricating the processing cover 24 is selecting a material that is less dense than the fluid collected in the processing vessel 12 while also being biocompatible and sterilizable.

The biocompatible and sterilizable polymeric materials typically have a density that is not less than the fluid collected in the processing vessel 12. It has been found that forming the processing cover 24 with a region that retains air is sufficient to cause the processing cover 24 to float on the fluid collected in the processing vessel 12.

The processing cover 24 includes an outer wall 40 having an outer diameter that is slightly smaller than the inner diameter of the processing vessel 12. Such a configuration enables the processing cover 24 to move vertically in the processing vessel 12.

Proximate at least one of the upper and lower ends of the outer wall 40, an extension 42 laterally extends therefrom. The extension 42 may enhance the ability of the processing cover 24 to vertically move in the processing vessel 12 without becoming wedged therein.

The processing cover 24 also includes a central wall member 44 that inwardly extends from the outer wall 40 intermediate the upper and lower edges of the processing cover 24. As illustrated in FIG. 3, the central member 44 may be closer to the lower edge than to the upper edge.

The connection port 46 is formed in the central wall member 44. The connection port 46 facilitates attachment of the tubing 16 to the processing cover 24. In certain embodiments, the connection port 46 utilizes a connection mechanism that facilitates attachment and detachment of the tubing 16 from the processing cover 24. An example of one such suitable mechanism is a luer lock.

An air-retaining region 48 is formed along a lower surface of the central member 44. The air-retaining region 48 decreases the overall density of the processing cover 24, which thereby enhances the ability of the processing cover 24 to float on top of the fluid in the processing vessel 12.

The air-retaining region 48 is a partially enclosed region along the lower surface of the central wall member 44. In particular, the air-retaining region 48 is elevated above the lower edge of the outer wall 40. The air-retaining region 48 is also elevated above an aperture in the lower surface of the central wall member 44 that is in communication with the connection port 46 as a result of a downwardly directed portion 49 of the central wall member 44. A distance at which the downwardly directed portion 49 extends downwardly from the lower surface of the central wall member 44 is a primary factor in the amount of air that can be retained in the air-retaining region 48 because trapped air at a distance that is greater than the downwardly directed portion 49 will pass out through the connection port 46.

The desired volume of the air-retaining region 48 is affected by factors such as the density of the material that is used in fabricating the processing cover 24 as well as the volume of the material that is used in fabricating the processing cover 24.

In certain embodiments, the placement of the central wall member 44 and the size of the air-retaining region 48 is selected so that the level of the liquid when the processing cover 24 is approximately intermediate between the upper and lower edges of the processing cover 24. Such a configuration may enhance the ability of the processing cover 24 to move generally vertically in the processing vessel 12.

To enhance the ability to accurately mold the processing cover 24, the central wall member 44 is formed with a thickness that is generally consistent over the surface thereof. Since no material is typically placed in the upper part of the processing cover 24, the shape of the upper side of the central wall member 44 does not impact the operation of the invention.

The lower surface of the central wall member 44 that extends between the air-retaining region 48 and the connection port 46 may be tapered upwardly (away from a lower surface of the processing cover 24) and inwardly (from the outer wall 40 toward the connection port 46). This configuration facilitates fluid flowing towards the connection port 46 as the vacuum causes the fluid to be withdrawn from the processing vessel 12. Forming the central wall member 44 with the upwardly and inwardly taper may enhance the ability to not only minimize withdrawing air through the connection port 46 but also maximize the amount of the desirable cells that are recovered while minimizing the amount of the red blood cells that are withdrawn from the processing vessel 12.

While it is illustrated that the connection port 46 is approximately at the center of the processing cover 24, a person of skill in the art will appreciate that alternative configurations may be used. Additionally, while the processing cover 24 is illustrated as having a single connection port 46, it is possible for the processing cover 24 to include more than one of the connection ports 46. While the processing vessel 12 and the processing cover 24 are both illustrated as having a generally circular profile, a person of skill in the art will appreciate that alternative configurations may be used, examples of which include oval, square or rectangular.

The tubing 16 may have a relatively small inner diameter such as between about 1 and about 5 millimeters. At least a portion of the tubing 16 may be fabricated from a transparent material to evaluate the characteristics of the material being withdrawn through the tubing 16. This combination of the tubing's relatively small inner diameter and the transparent nature facilitates separation of the beneficial components in the withdrawn tissue from the red blood cells, which will remain in the processing vessel 12 using the process, which is described in more detail herein.

The relatively small diameter and transparent nature of the tubing facilitates seeing changes in the properties of the liquid being drawn through the tubing 16. For example, after the addition of a red blood cell agglomerating material to the bone marrow in the processing vessel 12, the agglomerated red blood cells settle to a lower portion of the processing vessel 12 and such settled agglomerated red blood cells have a different color than the other portions of the bone marrow in the processing vessel 12. When withdrawing the liquid from the processing vessel 12, it is desirable to withdraw substantially all of the liquid other than the agglomerated red blood cells from the processing vessel 12 while substantially preventing the agglomerated red blood cells from passing into the bone void filler preparation container 14 to thereby recover a very high percentage of the progenitor cells from the bone marrow aspirate.

An end of the tubing 16 opposite the processing cover 24 engages a first port 30 on the bone void filler preparation container 14 such that fluid withdrawn from the processing vessel 12 passes through the bone void filler matrix in the bone void filler preparation container 14. In certain embodiments, the tubing 16 is removable attached to the first port 30 using a mechanism such as a luer lock.

A second port 32 on the bone void filler preparation container 14 is attached to a mechanism that is capable of utilizing a force to cause the liquid to be pulled through the tubing 16 and then flow through the bone void filler preparation container 14.

Because of the relatively small volume of the liquid in the processing vessel 12, a syringe 34 may be used to apply the force as a plunger is withdrawn therefrom. In another embodiment, the force is applied by a conventional vacuum system that is present in many medical facilities.

Using a syringe is one technique for associating the beneficial cells with the tricalcium phosphate. A benefit of using the syringe to cause the suction to be drawn on the second end of the bone void filler preparation container 14 is that a sufficient vacuum is applied to cause the bone marrow to be drawn through the tricalcium phosphate in the bone void filler preparation container 14 without the force being so great that the bone marrow is caused to form channels through the tricalcium phosphate.

The force is continued until a desired volume of the bone marrow is drawn through the tricalcium phosphate. In certain embodiments, substantially all of the red blood cell depleted material is withdrawn from the processing vessel 12. A benefit of this process is that the cells in the bone marrow are substantially unaffected and undamaged during the process of forming the bone void filler.

The bone void filler preparation container 14 may have a generally cylindrical shape. A length and a width of the bone void filler preparation container 14 are selected based upon the volume of the bone void filler that is desired to be prepared at a time. In certain embodiments, the bone void filler preparation container 14 facilitates placement therein of about 3 cubic centimeters of tricalcium phosphate.

In certain embodiments, a width of the bone void filler preparation container 14 is approximately the same as a length of the bone void filler preparation container 14. Using such a configuration enhances the ability of the bone marrow to flow through the bone void filler preparation container 14 while also facilitating substantially all of the beneficial cells in the bone marrow to be retained on the bone void filler in the bone void filler preparation container 14.

At least one of the ends 36 of the bone void filler preparation container 14 may be removably attached thereto to facilitate placing the material into the bone void filler preparation container 14 and then removing the bone void filler from the bone void filler preparation container 14. An example of one suitable mechanism for removably attaching the ends 36 to the bone void filler preparation container 14 is a screw-type mechanism.

One suitable configuration for the bone void filler preparation container 14 is illustrated in FIGS. 4-7. The bone void filler preparation container 14 includes a container base 50 to which a container cover 52 is removably attached.

The container base 50 includes a first end 54 and a second end 56. The first end 54 has a recess 58 formed therein. In certain embodiments the recess 58 has a generally cylindrical shape. A diameter of the recess 58 may be slightly larger proximate the first end 54 as compared to proximate the second end 56. Such a configuration not only facilitates molding of the container base 50 but also enhances the ability to remove the bone void filler from the bone void filler preparation container 14.

The recess 58 is preferably formed with an aspect ratio (height/width) that is greater than 1. In other embodiments, the aspect ratio is between about 2:1 and 4:1. Such a configuration enhances the ability to recover progenitor cells from the liquid as the liquid passes through the bone void filler preparation container 14.

The volume of the recess 58 is selected based upon the amount of bone void filler that is desired to be prepared. In certain embodiments, the volume of the recess 58 is up to about 10 cubic centimeters. In other embodiments, the volume of the recess 58 is between about 2 and 5 cubic centimeters.

Proximate the second end 56 in the recess, the container base 50 may include an indention 64 formed therein that is adapted to receive a particle retaining device 70 such as mesh that retains the particulate material used to fabricate the bone void filler. The mesh is fabricated with a particle size that depends on factors such as the granulation of the material that is placed in the container base 50.

Proximate the first end 54, the container base 50 includes a mechanism to facilitate attachment of the container cover 52 to the container base 50. In certain embodiments, the attachment mechanism is a thread that extends from an outer surface of the container base 50.

Proximate the second end 56, the base includes connection port 60 that is used to attach the bone void filler preparation container 14 to a device utilized to pull a vacuum to draw the fluid from the collection vessel 12. In certain embodiments, the connection port 60 has a standardized shape such as a luer lock, which provides a substantially water and air-tight connection between the components.

Intermediate the first end 54 and the second end 56, the container base 50 may have a mechanism that enhances the ability to grip the container base 50. An example of one suitable mechanism to enhance the ability to grip the container base 50 is at plurality of lugs 62.

The container cover 52 is capable of substantially sealing the container base 50 such that the only way for material to enter the bone void filler preparation container 14 is through a connection port 64 in the container cover 52. Similar to the connection port 60, the connection port 64 may utilize a standardized shape such as a luer lock, which provides a substantially water and air-tight connection between the components.

The container cover 52 includes an attachment mechanism that facilitates the container cover 52 removably engaging the container base 50. In certain embodiments the attachment mechanism is a thread that extends from an inner surface of the container cover 52. To enhance the ability to form a water and air-tight seal when the container cover 52 is attached to the container base 50, a resilient sealing mechanism 68 such as an O-ring may be utilized proximate the intersection of the container cover 52 and the container base, as illustrated in FIG. 5.

The container cover 52 may have a gripping mechanism that enhances the ability to grip the container cover 52 when moving the container cover 52 to and from engagement with the container base 50. An example of one suitable mechanism to enhance the ability to grip the container cover 52 is a plurality of lugs 66.

The configuration of the container cover 52 and the container base 50 may facilitate moving to and from engagement with each other using manual force so that tools are not needed to attach and detach the container cover 52 and the container base 50.

In certain embodiments, the bone void filler preparation container 14 is substantially filled with tricalcium phosphate. It has surprisingly been discovered that the recovery of the progenitor cells from the bone marrow increases when the average particle size of the tricalcium phosphate is above a threshold level.

The material in the bone void filler preparation container 14 also has an affinity for the beneficial components in the aspirate such that as the beneficial components flow past the material, the beneficial components are attached to the material. The beneficial components are thereby retained in the bone void filler preparation container 14 would be included in the bone graft fabricated therefrom. For example, the material may have an affinity for the connective tissue progenitor cells.

In certain embodiments, the material is a biomaterial. In other embodiments, the filter material is a naturally occurring biocompatible material. One such biomaterial is solid when dry but that solubilizes when wet. Examples of suitable materials are collagen materials such as are marketed under the designations Helitene and Avitene, which are conventionally used to stop bleeding in wounds. Additional materials could be configured from keratin, collagen, hyaluronic acid, chondroitin, glucosamine, amniotic fluid, tissue from an amniotic sac, or any other biocompatible material that may or may not be hydrogels.

The supernatant is passed through the bone void filler preparation container 14 relatively quickly to retain all or selectively retain specific cells like connective tissue progenitor cells, without absorbing the supernatant fluid. The second step would be hydration of the material such as using saline, phosphate-buffered saline and water to form a cell suspension.

Certain substances have an affinity for connective tissue progenitor cells, which causes the selective cell retention. It is believed that this affinity may be associated with a surface charge of the connective tissue progenitor cells, which relates to zeta potential.

As used herein, passing the supernatant relatively quickly through the bone void filler preparation container 14 means the process takes less than about five minutes. In certain embodiments, the supernatant passes through the bone void filler preparation container 14 in between about 60 and 90 seconds.

In another embodiment, the connective tissue progenitor cells are bound to a biopolymer, an example of which is keratin, to form a therapeutic composition. The product thereby produced not only benefits from the advantageous properties of the connective tissue progenitor cells but also benefits from the advantageous properties of the keratin.

It is also possible to use the connective tissue progenitor cells in conjunction with cells that are obtained from amniotic fluid and/or other portions of the amniotic sac. These components may be used alone or in conjunction with at least one biopolymer, an example of which is keratin.

In certain embodiments, the product thereby produced is in the form of hydrogel fibers or hydrogel beads. This product is suitable for use in a variety of applications, examples of which include bone graft and the compounds that are efficacious in treating soft tissue conditions, which are discussed in more detail in other portions of this patent application.

Another advantage of this configuration is that a small amount of filter material such as in the range of between about 1-2 cubic centimeters could be used to capture the cells with very high efficiency. As used herein, very high efficiency means that greater than about 70 percent by weight of the aspirated connective tissue progenitor cells are captures and, in certain embodiments, greater than about 90 percent by weight of the aspirated connective tissue progenitor cells are captured.

In still another embodiment, it is possible to use biomaterial hybrid materials such as combinations of keratin and at least one of tricalcium phosphate, poly-lactic acid, poly-glycolic acid, poly-caprolactone and hyaluronic acid. These materials may be used in a variety of forms, examples of which include fiber and granular.

Figure 8:
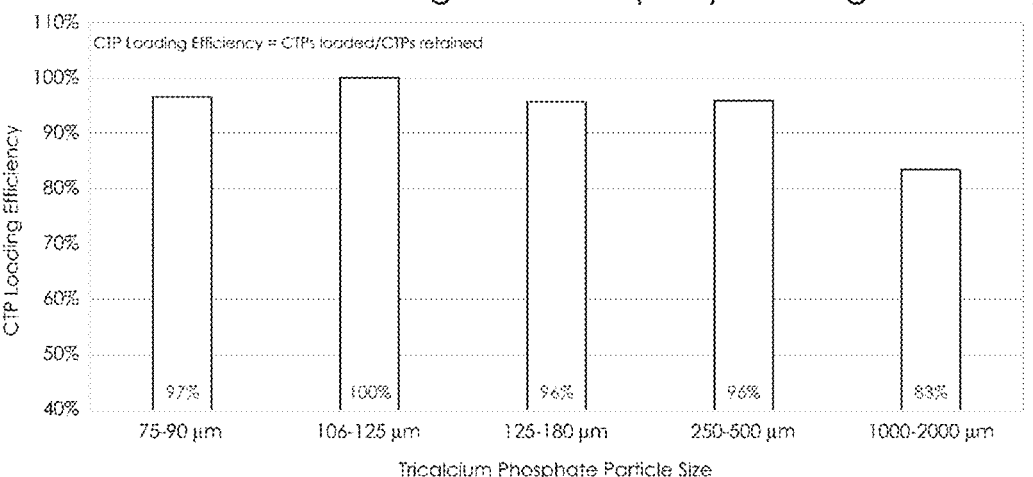
FIG. 8 is a graph of connective tissue progenitor cell loading efficiency for tricalcium phosphate having different particle sizes.

FIG. 8 illustrates that the loading efficiency, which is the number of progenitor cells retained to the number of progenitor cells loaded, remains relatively consistent between 96 percent and 100 percent to the samples done using tricalcium phosphate having an average particle sizes of 75-90 μm, 106-125 μm, 125-180 μm and 250-500 μm. The loading efficiency decreased to 83 percent for the sample using tricalcium phosphate having an average particle size of 1,000-2,000 μm. It is anticipated that other bone graft matrices such as autograft, allograft, xenograft, calcium sulphate, hydroxyapatite, polymers, ceramics, collagen and combinations thereof would exhibit similar results.

Such a result is anticipated because the larger particle size tricalcium phosphate would have bigger openings between the particles through which the progenitor cells would pass rather than becoming associated with the tricalcium phosphate and thereafter being retained in the bone void filler preparation container 14.

Figure 9:
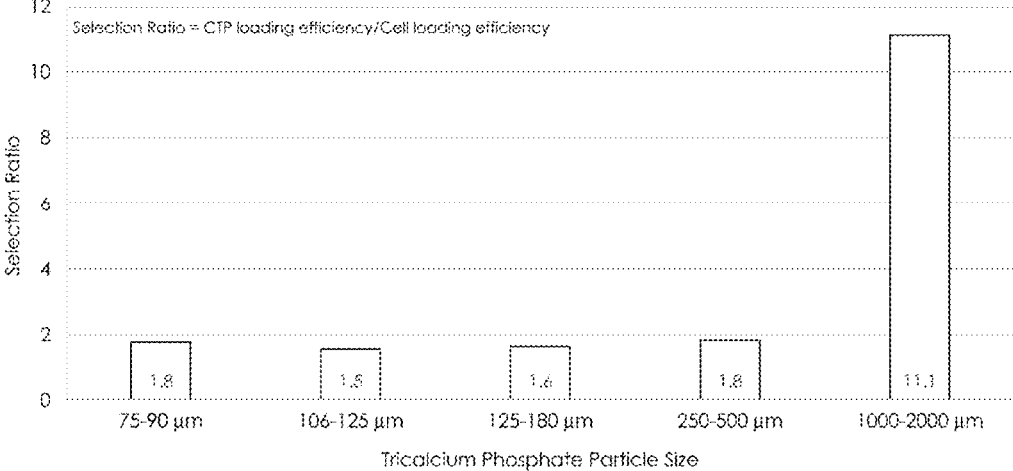
FIG. 9 is a graph of connective tissue progenitor cell selection ratio for tricalcium phosphate having different particle sizes.

One technique for evaluating the recovery of the progenitor cells from the bone marrow is the selection ratio, which is the ratio of the connective tissue progenitor cell loading efficiency to the total nucleated cell loading efficiency. As illustrated in FIG. 9, the selection ratio is between 1.5 and 1.8 when the tricalcium phosphate is used at average particle sizes of 75-90 μm, 106-125 μm, 125-180 μm and 250-500 μm. When the tricalcium phosphate average particle size is increased to 1,000-2,000 μm, the selection ratio increased to 11.1. Such a result is more than five times greater than the selection ratio of the smaller particle size tricalcium phosphate samples. It is anticipated that other bone graft matrices such as autograft, allograft, xenograft, calcium sulphate, hydroxyapatite, polymers, bioresorbable polymers, amniotic membrane, dehydrated amniotic fluid, keratin, bioactive glass matrices, chondroitin, ceramics, collagen and combinations thereof would exhibit similar results.

Based upon results of the four smaller particle sizes all being in the range of 1.5 to 1.8, a person of skill in the art would have expected the selection ratio for the largest particle size to also be in the range of 1.5 to 1.8. Alternatively, a person of skill in the art would have expected the selection ratio to decrease if the considerably larger particles provided a less efficient capture of the progenitor cells.

The preceding result is thereby unexpected in that a significantly higher percentage of the progenitor cells are retained on the larger particle size tricalcium phosphate particles. As discussed above, because of the challenges in extracting the bone marrow, it is desired to maximize the percentage of the beneficial progenitor cells in the bone marrow that are aspirated from the patient. These results were achieved in spite of there being a lower overall recovery of the cells in the bone marrow.

In certain embodiments, the selection ratio of greater than about 3 represents a significant improvement over the prior art. In other embodiments, the selection ratio is greater than about 10, which represents a substantial improvement over the prior art.

Based upon the preceding results, the explanation for the larger size tricalcium phosphate particles providing the significantly higher selection ratio is that the surface area of the larger size particles facilitates greater selective retention of the progenitor cells on the surface of the tricalcium phosphate particles even though the large particle size tricalcium phosphate exhibits an overall retention that is lower than is obtained with the smaller particle size tricalcium phosphate. It is anticipated that other bone graft matrices such as autograft, allograft, xenograft, calcium sulphate, hydroxyapatite, polymers, bioresorbable polymers, amniotic membrane, dehydrated amniotic fluid, keratin, bioactive glass matrices, chondroitin, ceramics, collagen and combinations thereof would exhibit similar results.

It is expected that larger particle size tricalcium phosphate would also produce advantageous results. Such larger size particles would likely produce similar results up to about 5,000 μm. In view of the preceding results, the tricalcium phosphate has a particle size of between about 500 μm and about 4,000 μm. In other embodiments, the tricalcium phosphate has a particle size of between about 600 μm and about 3,000 μm. In still other embodiments, the tricalcium phosphate has a particle size of between about 750 μm and about 2,000 μm. It is anticipated that other bone graft matrices such as autograft, allograft, xenograft, calcium sulphate, hydroxyapatite, polymers, ceramics, collagen and combinations thereof would exhibit similar results.

As an alternative to using particulate tricalcium phosphate, it is also possible to form the tricalcium phosphate into shapes having the beneficial particle sizes that are discussed above and achieve results that are similar to the results set forth above.

The tricalcium phosphate may have a multi-strata configuration. In certain embodiments, the tricalcium phosphate is configured to go from high inherent porosity proximate the inlet to lower inherent porosity proximate the outlet. Alternatively, it may be possible to use a reverse descending strata configuration to help keep the smallest particles in place. In both of the preceding configurations, the tricalcium phosphate may have a particle size of between about 1,000 μm and 2,000 μm.

In addition to using the bone void filler as prepared above, it is possible to mix the bone void filler with at least one additional component prior to use. For example, if bone fragments were collected as discussed above, the bone fragments may be mixed with the bone void filler to modify the properties of the bone void filler. For example, it is possible to add tricalcium phosphate having a smaller particle size. A person of skill in the art will appreciate that a variety of bone graft matrices may also be used. The bone graft matrix should be a cell binding and cell friendly, osteoconductive material. The matrix can be allogeneic, synthetic or a combination thereof. The allogeneic material can be provided in a variety of forms. Examples of two such suitable forms are granules and fibers.

While the preceding discussion is with respect to the use of tricalcium phosphate to prepare the bone void filler, it is possible to use a variety of other matrices to prepare the bone void filler according to the invention.

Using such a process, a surgeon is able to obtain the benefits associated with using a bone graft that contains the beneficial cells while at the same time being able to use a primary bone graft material that the surgeon prefers.

The bone graft base may be fabricated with a relatively low viscosity such that when the bone graft base is mixed with the primary bone graft material, the bone graft thereby produced has a desired viscosity. The concentration of the bone graft base in the bone graft may be between about 10 percent and about 90 percent. In other embodiments, the concentration of the bone graft base in the bone graft is between about 20 percent by weight and about 50 percent by weight.

The viscosity of the bone void filler can be adjusted by changing the amount of water in the bone marrow aspirate concentrate as well as the amount of water that is allowed to pass through the filter membrane at the second end of the bone void filler preparation container 14.

Because of the intended in-vivo use of the bone graft, the bone void filler should be provided in a sterile configuration to minimize the potential of introducing pathogens during the process of implanting the bone void filler. Prior to using the bone void filler, the components used to fabricate the bone void filler should be relatively uniformly mixed.

Alternatively to applying the bone void filler as a paste, it is possible to form the bone void filler material into the desired shape of the implant. After the bone void filler material is formed into the desired shape, the moisture content of the bone void filler material can be reduced to cause the implant to become more rigid. An example of one technique that may be used to reduce the moisture content of the implant is heating.

The physical properties of the bone graft material may be enhanced by the addition of at least one additive to the bone void filler material. An example of one additive is collagen.

The total time from harvesting of the cells from the patient to having a bone void filler that is ready for use in the patient or is used in the patient as a bone void filler can be done in a relatively short period of time. In certain embodiments, the process takes less than one hour. In other embodiments, the process takes between about 30 minutes and about 40 minutes.

Another advantage of the system described herein is that it is a closed system. Such a closed system facilitates use of the osteomedullary tissue processing system in non-sterile environments such as a doctor's office, as compared to a sterile environment that is typically only found in an operating room.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A process of preparing bone void filler comprising:
providing a processing vessel having a recess formed therein;
providing a processing cover that comprises:
an outer wall having an upper edge and a lower edge,
a central wall member that extends inwardly from the outer wall intermediate the upper and lower edges of the processing cover, wherein the central wall member has an aperture formed therein and wherein the central wall member has a downwardly directed portion that defines an air retaining region that is closer to the outer wall upper edge than the aperture, and
a connection port that is operably is connected to the aperture;
providing a bone void filler preparation container comprising an inlet portion and an outlet port;
fluidly connecting the processing cover connection port and the bone void filler preparation container inlet port with tubing;
placing bone void filler matrix in the bone void filler preparation container;
placing bone marrow aspirate in the processing vessel;
placing the processing cover in the processing vessel so that air is retained in the air-retaining region and so that at least a portion of the processing cover is above an upper surface of the bone marrow aspirate;
using the bone void filler preparation container outlet port to draw the bone marrow aspirate through the processing cover aperture, the tubing and the bone void filler matrix; and
retaining progenitor cells from the bone marrow aspirate in the bone void filler matrix to form bone void filler.

2. The bone void filler preparation process of claim 1, wherein as bone marrow aspirate is withdrawn from the processing vessel, the processing cover moves in the processing vessel and the air is retained in the air-retaining region.

3. The bone void filler preparation process of claim 1, and further comprising separating red blood cells from the bone marrow aspirate to form a red blood cell depleted bone marrow aspirate, wherein the red blood cell depleted bone marrow aspirate is withdrawn from the processing vessel.

4. The bone void filler preparation process of claim 1, wherein the outer wall has a shape that is similar to a shape of the processing vessel recess, wherein the outer wall has a size that is similar to a size of the processing vessel recess and wherein the processing vessel recess is generally cylindrical.

5. The bone void filler preparation process of claim 1, wherein the processing cover move in a vertical direction with respect to the processing vessel, wherein the processing cover has a density that is less than a density of the bone marrow aspirate in the processing vessel, wherein the downwardly directed portion is formed along a lower surface of the central wall member and wherein the air-retaining region is elevated from the outer wall lower edge.

6. The bone void filler preparation process of claim 1, and further comprising positioning the central wall member between the upper and lower edges of the outer wall and selecting a size of the air-retaining region so that an upper surface of the bone marrow aspirate in approximately intermediate the upper and lower edges of the outer wall when the processing cover is placed in the processing vessel.

7. The bone void filler preparation process of claim 1, wherein a portion of a lower surface of the central wall member that extends between the air-retaining region and the aperture tapers upwardly towards the outer wall upper edge and inwardly from the outer wall to the aperture to facilitate flow of the bone marrow aspirate towards the aperture.

8. The bone void filler preparation process of claim 1, and further comprising:

provide a first extension that extends from an outer surface of the outer wall proximate the outer wall upper edge;

providing a second extension that extends from the outer surface of the outer wall proximate the outer wall lower edge; and restricting the processing cover to moving in a vertical direction in the processing vessel with the first extension and the second extension.

9. A process of preparing bone void filler comprising:

providing a processing vessel having a recess formed therein;

providing a processing cover that comprises:

an outer wall having an upper edge and a lower edge, a central wall member that extends inwardly from the outer wall intermediate the upper and lower edges of the outer wall and wherein the central wall member has an aperture formed therein, a connection port, that is operably connected to the aperture, a first extension that extends from an outer surface of the outer wall proximate the outer wall upper edge, and a second extension that extends from the outer surface of the outer wall proximate the outer wall lower edge providing a bone void filler preparation container comprising an inlet portion and an outlet port;

fluidly connecting the processing cover connection port and the bone void filler preparation container inlet port with tubing;

placing bone void filler matrix in the bone void filler preparation container;

placing bone marrow aspirate in the processing vessel;

placing the processing cover in the processing vessel so that air is retained in the air-retaining region and so that at least a portion of the processing cover is above an upper surface of the bone marrow aspirate;

restricting the processing cover to moving in a vertical direction in the processing vessel with the first extension and the second extension;

using the bone void filler preparation container outlet port to draw the bone marrow aspirate through the processing cover aperture, the tubing and the bone void filler matrix; and retaining progenitor cells from the bone marrow aspirate in the bone void filler matrix to form bone void filler.

10. The bone void filler preparation process of claim 9, wherein the central wall member has a downwardly directed portion that defines an air-retaining region, wherein the air-retaining region is closer to the outer wall upper edge than the aperture and wherein as bone marrow aspirate is withdrawn from the processing vessel, the processing cover moves in the processing vessel and the air is retained in the air-retaining region.

11. The bone void filler preparation process of claim 9, and further comprising separating red blood cells from the bone marrow aspirate to form a red blood cell depleted bone marrow aspirate, wherein the red blood cell depleted bone marrow aspirate is withdrawn from the processing vessel.

12. The bone void filler preparation process of claim 9, wherein the outer wall has a shape that is similar to a shape of the processing vessel recess, wherein the outer wall has a size that is similar to a size of the processing vessel recess, wherein the processing vessel recess is generally cylindrical, wherein the processing cover has a density that is less than a density of the bone marrow aspirate in the processing vessel, wherein the downwardly directed portion is formed along a lower surface of the central wall member and wherein the air-retaining region is elevated from the outer wall lower edge.

13. The bone void filler preparation process of claim 9, and further comprising positioning the central wall member between the upper and lower edges of the outer wall and selecting a size of the air-retaining region so that an upper surface of the bone marrow aspirate in approximately intermediate the upper and lower edges of the outer wall when the processing cover is placed in the processing vessel.

14. The bone void filler preparation process of claim 9, wherein a portion of a lower surface of the central wall member that extends between the air-retaining region and the aperture tapers upwardly towards the outer wall upper edge and inwardly from the outer wall to the aperture to facilitate flow of the bone marrow aspirate towards the aperture.

15. A bone void filler preparation system comprising:

a processing vessel having a recess formed therein, wherein the processing vessel is adapted to receive bone marrow aspirate;

a processing cover that comprises:

an outer wall having an upper edge and a lower edge;

a central wall member extends inwardly from the outer wall intermediate the upper and lower edges of the outer wall, wherein the central wall member has an aperture formed therein;

a first extension extends from an outer surface of the outer wall proximate the outer wall upper edge;

a second extension extends from the outer surface of the outer wall proximate the outer wall lower edge, wherein the first extension and the second extension restrict the processing cover to moving in a vertical direction in the processing vessel; and a connection port is operably connected to the aperture, wherein the processing cover is movable in the processing cover recess;

a bone void filler preparation container comprising an inlet portion and an outlet port, wherein the bone void filler preparation container is adapted to receive a bone void filler matrix therein; and tubing that fluidly connects the processing cover connection port and the bone void filler preparation container inlet port.

16. The bone void filler preparation system of claim 15, wherein the outer wall has a shape that is similar to a shape of the processing vessel recess, wherein the outer wall has a size that is similar to a size of the processing vessel recess, wherein the processing vessel recess is generally cylindrical and wherein the processing cover is slidable in a vertical direction with respect to the processing vessel.

17. The bone void filler preparation system of claim 15, wherein the processing cover has a density that is less than a density of the bone marrow aspirate in the processing vessel.

18. The bone void filler preparation system of claim 15, wherein the central wall member further comprises a downwardly directed portion that defines an air-retaining region and wherein the air-retaining region is closer to the outer wall upper edge than the aperture.

19. The bone void filler preparation system of claim 18, wherein the downwardly directed portion is formed along a lower surface of the central wall member, wherein the air-retaining region is elevated from the outer wall lower edge and wherein a portion of a lower surface of the central wall member that extends between the air-retaining region and the aperture tapers upwardly towards the outer wall upper edge and inwardly from the outer wall to the aperture.

20. The bone void filler preparation system of claim 18, wherein when the bone marrow aspirate is in the processing vessel, a position of the central wall member between the upper and lower edges of the outer wall and a size of the air-retaining region are selected so that an upper surface of the bone marrow aspirate in approximately intermediate the upper and lower edges of the outer wall.

* * * * *